United States Patent

Peters et al.

[11] Patent Number: 5,453,160
[45] Date of Patent: Sep. 26, 1995

[54] USE OF MIXED POLYOXYPROPYLENE GLYCOLS IN THE EXTRACTIVE DISTILLATION OF PROPYLENE OXIDE

[75] Inventors: Michael W. Peters, Austin; William K. Culbreth, III, Beaumont; Mark A. Mueller, Austin, all of Tex.

[73] Assignee: Texaco Chemical Inc., White Plains, N.Y.

[21] Appl. No.: 251,151

[22] Filed: May 31, 1994

[51] Int. Cl.$^6$ .......................... B01D 3/40; C07D 301/32
[52] U.S. Cl. ................... 203/64; 203/78; 203/80; 203/DIG. 9; 549/541
[58] Field of Search .................. 203/64, 14, 78, 203/80, 84, DIG. 9, DIG. 23; 549/541, 542

[56] References Cited

U.S. PATENT DOCUMENTS

| | | | |
|---|---|---|---|
| 3,578,568 | 5/1971 | Washall | 203/64 |
| 4,297,287 | 10/1981 | Costantini et al. | 549/518 |
| 4,402,794 | 9/1983 | Nemet-Maurodin et al. | 203/70 |
| 5,000,825 | 3/1991 | Shih et al. | 203/64 |
| 5,129,996 | 7/1992 | Shih | 203/64 |
| 5,139,622 | 8/1992 | Marquis et al. | 203/64 |
| 5,145,563 | 9/1992 | Culbreth, III et al. | 203/64 |
| 5,154,803 | 10/1992 | Marquis et al. | 203/64 |
| 5,154,804 | 10/1992 | Marquis et al. | 203/14 |
| 5,160,587 | 11/1992 | Marquis et al. | 203/14 |
| 5,262,017 | 11/1993 | Meyer et al. | 203/70 |
| 5,340,446 | 8/1994 | Nelson et al. | 203/64 |

OTHER PUBLICATIONS

CA 76: 34601.

*Primary Examiner*—Virginia Manoharan
*Attorney, Agent, or Firm*—James L. Bailey; Kenneth R. Priem; Carl G. Ries

[57] ABSTRACT

An extractive distillation agent comprising a mixture of polyoxypropylene glycols is fed to an extractive distillation column used for the distillation of propylene oxide contaminated with water, acetone and methanol to obtain an overhead distillate anhydrous propylene oxide fraction contaminated with reduced quantities of methanol and a heavier bottoms distillation fraction containing the polyoxypropylene glycols, water and acetone and some of the methanol introduced into the distillation column.

5 Claims, 1 Drawing Sheet

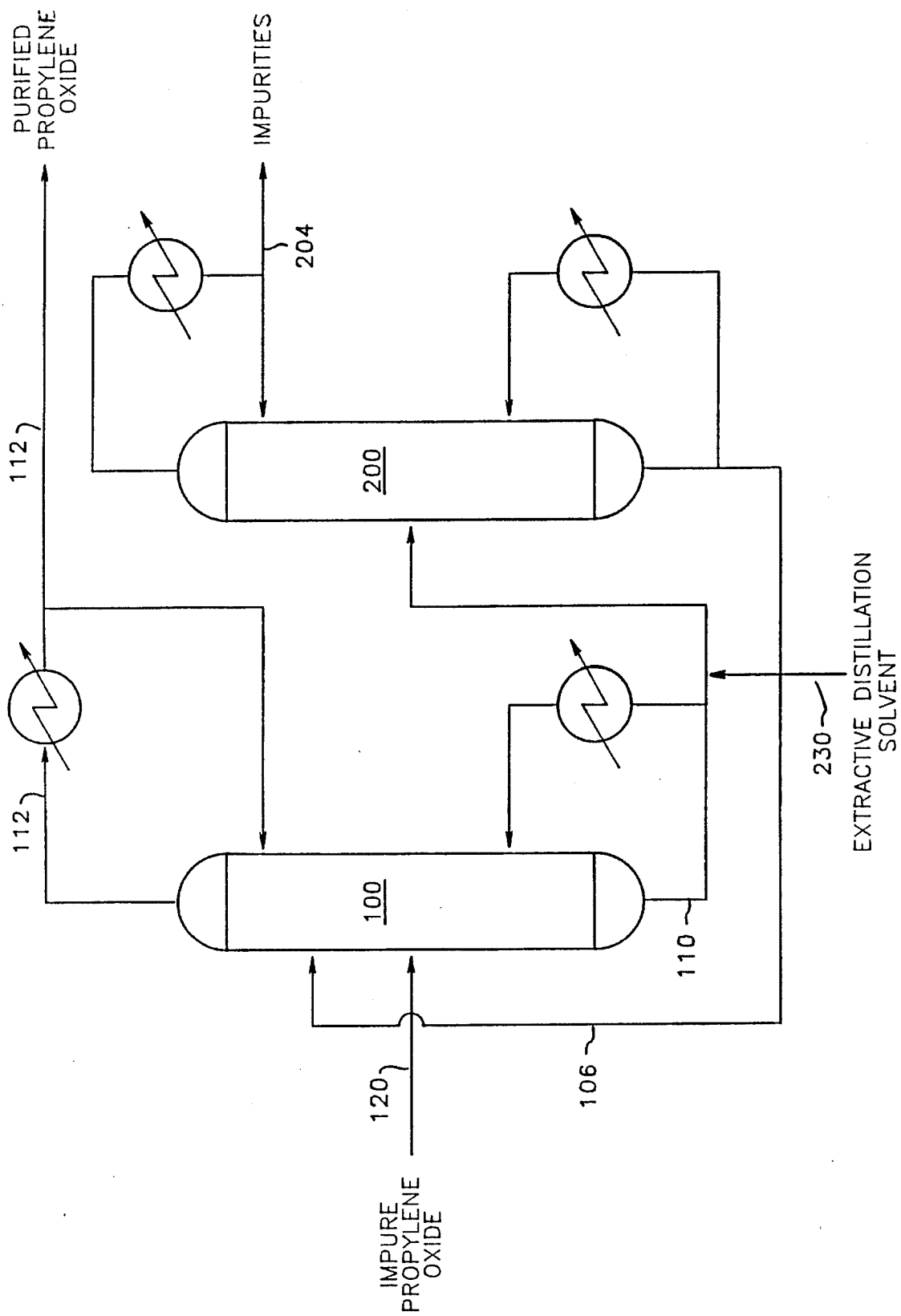

USE OF MIXED POLYOXYPROPYLENE GLYCOLS IN THE EXTRACTIVE DISTILLATION OF PROPYLENE OXIDE

BACKGROUND OF THE INVENTION

1. Technical Field of the Invention

This invention relates to the purification of propylene oxide. More particularly, this invention relates to a distillation process for removing contaminating quantities of impurities including oxygen-containing impurities such as methanol, acetone and water from an impure propylene oxide feedstock. Still more particularly, this invention relates to a method wherein an impure propylene oxide feedstock, such as a feedstock contaminated with from about 50 to about 4,000 ppm of methanol, from about 0.01 to about 2 wt. % of water and from about 0.01 to about 2 wt. % of acetone is purified in an extractive distillation column using a mixture of polyoxypropylene glycol as an extractive distillation agent.

2. Prior Art a) General Background Information

It is known to react a hydroperoxide feedstock such as tertiary butyl hydroperoxide with propylene in the presence of an epoxidation catalyst in order to provide a reaction product comprising propylene oxide, an alcohol corresponding to the hydroperoxide feedstock, a solvent, and impurities (see, for example, Kollar U.S. Pat. No. 3,350,422, Kollar U.S. Pat. No. 3,351,635 and Sorgenti U.S. Pat. No. 3,666,777.

It is also known to separate the reaction product by distillation in order to obtain a plurality of fractions including, for example, a propylene recycle fraction, a propylene oxide product fraction, an alcohol fraction, etc.

It is also known that methanol, acetone and water are common contaminants for propylene oxide which are removed only with difficulty.

For example, Mitchell et al. U.S. Pat. No. 2,550,847 is directed to a process for separating purified propylene oxide from a crude propylene oxide product contaminated with acetaldehyde, methyl formate, methanol, etc., by treating the crude mixture with an aqueous basic substance followed by recovery of the purified propylene oxide by any suitable means such as by decantation. Mitchell et al. reported a recovery of a product containing 78 to 82 wt. % of propylene oxide which, they stated, could be increased in purity to about 95 to 99% by fractional distillation.

b) Extractive Distillation Background

Robeson et al. U.S. Pat. No. 2,622,060 discloses a process for the purification of propylene oxide contaminated with impurities, including methanol, by subjecting the impure propylene oxide to distillation in the presence of an extractive distillation agent comprising an aqueous solution of an alkali. The inventors report in Example 1 of their patent a method wherein 500 parts by weight of a crude propylene oxide fraction was extractively distilled in accordance with their invention to obtain 325 parts by weight of a product containing about 99.6 wt. % of propylene oxide. Thus, a significant loss of propylene oxide occurred during the process.

In a process unrelated to the purification of propylene oxide, Goddin et al. in U.S. Pat. No. 2,751,337 disclose a process for separating acetone from a mixture of acetone with methanol and methyl acetate utilizing water as an extractive distillation agent.

Hamlin et al. in U.S. Pat. No. 3,409,513 disclose the hydro-extractive distillation of mixtures comprising acetone, lower aliphatic alcohols and esters of lower aliphatic alcohols with carboxylic acids. It is pointed out by the patentees that acetone, methyl acetate and methanol form an azeotrope boiling at 55.5°–56.5° C. Williams et al. propose to recover partially purified acetone from such a ternary azeotrope by liquid-liquid extraction with water followed by hydro-extractive distillation of the aqueous phase in order to obtain a partially purified acetone fraction.

Hoorl and Newman U.S. Pat. No. 3,632,482 is directed to a propylene oxide recovery process by extractive distillation using an alcohol-ketone-hydrocarbon solvent. The invention relates to a method for the purification of crude propylene oxide contained in a mixture produced by the epoxidation of propylene with an organic hydroperoxide and calls for extractive distillation of the crude propylene oxide in a plurality of successive extractive distillation zones with the aid of a solvent mixture consisting essentially of hydrocarbons, alcohols, and/or ketones corresponding to the organic hydroperoxide employed in producing the propylene oxide. In the preferred embodiment of their invention, the extractive distillation agent is a recycle fraction from a three column distillation sequence wherein the bottoms from the third distillation column are flashed to obtain an overhead composed of hydrocarbons, alcohols and/or ketones which is recycled as an extractive distillation agent to the three distillation columns involved in the propylene oxide purification sequence.

Burns et al. U.S. Pat. No. 3,715,284 discloses a process for the purification of impure propylene oxide using acetone or a mixture of acetone with methanol which is introduced into a distillation column either below or together with the impure propylene oxide.

Schmidt U.S. Pat. No. 3,881,996 is directed to a distillation sequence employing at least three and optionally four columns for the purification of crude propylene oxide, one of the columns optionally being an extractive distillation column wherein a hydrocarbon such as octane is used as the extractive distillation agent.

Schmidt U.S. Pat. No. 4,140,588 discloses a process for the purification of propylene oxide contaminated with methanol and acetone using water as an extractive distillation agent, the water being introduced into the distillation column above the point of introduction of the crude propylene oxide feed.

Schmidt states at column 2, lines 50–55 that: "Propylene oxide, however, has a substantial solubility in water and is readily hydrolyzed to propylene glycol (PG) in the presence of large amounts of water"—i.e., in the reboiler section of the tower.

U.S. Pat. No. 4,971,661 discloses the use of an aqueous acetone extraction to remove methanol from propylene oxide.

U.S. Pat. No. 3,607,669 discloses the use of a $C_8$ to $C_{12}$ hydrocarbon to separate propylene oxide from water.

Yeakey et al. disclose the use of 2-hydroxyethyl 2-hydroxyethyl carbamate as an extractive distillation agent for the removal of water from impure propylene oxide in U.S. Pat. No. 5,116,465.

U.S. Pat. No. 5,116,466 to Marquis et al. discloses that one may use 1-methyl-2-pyrrolidinone as an extractive distillation agent to remove water, acetone and methanol from propylene oxide contaminated with these impurities.

U.S. Pat. No. 5,116,467 to Marquis et al. discloses the use of sulfolane as an extractive distillation agent to remove water from propylene oxide.

U.S. Pat. No. 5,145,561 to Marquis et al. discloses the use of ethylene carbonate and/or propylene carbonate as an extractive distillation agent to remove water from propylene oxide.

Culbreth et al. disclose the use of glycerol-1,3-di-t-butyl ether as an extractive distillation agent for the removal of water from impure propylene oxide in U.S. Pat. No. 5,145,563.

c. Glycol and Glycol Ether Extractants

Washall U.S. Pat. No. 3,578,568 discloses a process for removing oxygen-containing impurities such as acetone, acetaldehyde and methanol from impure propylene oxide using a glycol such as ethylene glycol or propylene glycol as an extractive distillation agent. It is stated that the concentration of the solvent in the vapor space in the extractive distillation zone of the extractive distillation tower should preferably be between 15 and 50 mole percent of the total vapor.

Shih et al. U.S. Pat. No. 5,000,825 discloses the purification of monoepoxides such as propylene oxide that are contaminated with oxygenated impurities such as water, low molecular weight alcohols, low molecular weight ketones, low molecular weight aldehydes and the like by the extractive distillation of the contaminated monoepoxide using a lower glycol containing 2 to 4 carbon atoms. Examples of the lower glycols that are given in the patent include ethylene glycol, 1,2-propane diol, 1,3-propane diol, 1,4-butane diol, 1,2-butane diol, 1,3-butane diol, 1,4-butane diol, butane diol and 2,3-butane diol. It is stated that higher diols or higher glycol ethers do not provide sufficient selectivity for the removal of impurities and they are not included in the list of extractive distillation solvents suitable for use in the invention.

In Marquis et al. U.S. Pat. No. 5,139,622 the use of triethylene glycol is disclosed for the removal of methanol, acetone and water from propylene oxide contaminated with these impurities.

Marquis et al. U.S. Pat. No. 5,154,803 discloses the use of 2-methyl-2,4-pentane diol as an extractive distillation agent in the removal of methanol, acetone and water from propylene oxide contaminated with these impurities.

Marquis et al. U.S. Pat. No. 5,154,804 discloses the use of monohydroxy alkoxy alkanols containing 5 to 8 carbon atoms as extractive distillation agents in the removal of methanol, acetone and water from propylene oxide contaminated with these impurities.

The use of dipropylene glycol as an extractive distillation agent for the removal of methanol, acetone and water from propylene oxide contaminated with these impurities is disclosed in Marquis et al. U.S. Pat. No. 5,160,587.

SUMMARY OF THE INVENTION

In accordance with the present invention, an impure propylene oxide feedstock, such as a feedstock contaminated with 0.01 to 2 wt. % of water, from about 50 to about 4,000 ppm of methanol and from about 0.01 to about 2 wt. % of acetone, is charged to the lower half of an extractive distillation column containing at least about 10 theoretical plates and an extractive distillation agent comprising a mixture of polyoxypropylene glycols is charged to the tower at a point at least 4 stages above the impure propylene oxide feed point. Preferably, the extractive distillation tower will contain from about 30 to about 120 theoretical plates and the extractive distillation agent will be charged to the tower at a point of from 7 to 50 theoretical stages above the impure propylene oxide feed point. The extractive distillation agent is introduced into the extractive distillation column in the ratio of said feedstock to said extractive distillation agent of from about 1:1 to about 20:1, and more preferably 2:1 to 10:1, whereby a light distillate fraction is obtained consisting essentially of propylene oxide contaminated with significantly reduced amounts of water, methanol and acetone, such as about 5 to about 600 ppm of water, about 15 to 2,000 ppm of methanol and about 0.1 to about 100 ppm of acetone.

BACKGROUND OF THE PRESENT INVENTION

When propylene is reacted in liquid phase with an organic hydroperoxide such as tertiary butyl hydroperoxide in solution in a solvent such as tertiary butyl alcohol in the presence of a soluble epoxidation catalyst such as a molybdenum epoxidation catalyst, a reaction mixture is formed comprising propylene oxide, an alcohol corresponding to the organic hydroperoxide feedstock and impurities including water and other oxygenated impurities such as methyl formate, acetaldehyde, acetone and methanol.

Propylene oxide is a hygroscopic substance, so that water is removed only with difficulty. It is important to remove as much of the water as possible, however, because the water present in the propylene oxide will tend to react with the propylene oxide to form propylene glycol.

It is also important to reduce the level of other oxygenated contaminants such as methanol and acetone to the lowest reasonably attainable level.

In accordance with conventional practice, an epoxidation reaction product formed by the molybdenum-catalyzed reaction of propylene oxide with tertiary butyl hydroperoxide in solution in tertiary butyl alcohol is separated into the principle components by distillation so as to form distillation fractions including a propylene distillation fraction, a propylene oxide distillation fraction, a tertiary butyl alcohol distillation fraction and a heavy distillation fraction containing the molybdenum catalyst and other products and by-products of the epoxidation reaction. However, the distillation fractions that are thus-obtained are characterized by the inclusion of impurities and, normally, must be further treated if commercially acceptable products are to be obtained. This is especially true for a propylene oxide distillation fraction contaminated with water and oxygenated contaminants including methanol and acetone.

It has been surprisingly discovered in accordance with the present invention that substantially all of the water initially present in a contaminated propylene oxide feedstock can be removed therefrom when the propylene oxide feedstock is extractively distilled in the presence of an extractive distillation agent comprising a mixture of polyoxypropylene glycols. Even more surprising is our discovery that substantially all of the acetone and most of the methanol present in the contaminated feedstock can also be removed from the propylene oxide when using a mixture of the polyoxypropylene glycols as the extractive distillation agent.

THE MIXED POLYOXYPROPYLENE GLYCOL EXTRACTIVE DISTILLATION AGENT

It has been discovered in accordance with the present invention that propylene oxide will react to a limited extent with propylene glycol and lower molecular weight polyoxypropylene glycols under the conditions of temperature, pressure and acidity, as defined herein, that exist in a propylene oxide extractive distillation column. It has been found that when propylene oxide is purified by distillation in the manner described herein, the liquid portion of the mixture of solvent and impure propylene oxide in the distillation column will be mildly acidic. As a consequence, when a propylene glycol such as monopropylene glycol, dipropylene glycol, tripropylene glycol or a mixture thereof is used as the extractive distillation solvent, a small amount of the propylene oxide in the distillation column will react with the propylene glycol extractive distillation solvent to form a propylene oxide adduct, which in turn can react with propylene oxide. As a consequence, the average molecular weight and composition of the resultant mixture of polyoxypropylene glycols will progressively change during the continuous extractive distillation of the impure propylene oxide.

It has been further surprisingly discovered in accordance with the present invention that during continuous extractive distillation operations a circulating stream of solvent having a substantially uniform concentration of components can be arrived at by purging a portion of the circulating stream of solvent and by replacing the purged portion of the circulating stream of solvent with an equivalent volume of fresh solvent. Thus, if about 0.1 to about 15 vol. % per hour of the total volume of circulating solvent is removed and replaced with an equivalent volume of fresh solvent, a circulating stream of solvent can be obtained in which not more than about 5 to about 35 wt. % of the circulating stream of solvent will have a molecular weight of more than about 250.

It has been still further surprisingly discovered in accordance with the present invention that the efficiency of the extractive distillation process is not impaired by the build-up of progressively larger quantities of the higher molecular weight polyoxypropylene glycols. Thus, it has been discovered that even though the di-, tri-, tetra- and penta-polyoxypropylene glycols have different physical characteristics (e.g., boiling point, molecular weight, freezing point, etc.) they exhibit substantially identical extractive distillation characteristics when used in admixture in accordance with the present invention.

When propylene oxide is reacted with propylene glycol to provide di-propylene glycol, the reaction product will actually comprise a mixture of isomers, as follows:

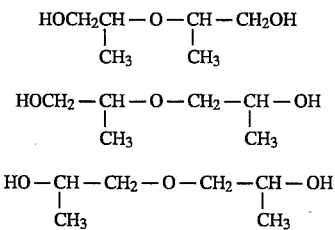

Dipropylene glycol is a colorless, hygroscopic, practically odorless liquid having a boiling point of 231.8° C., a vapor pressure of less than 0.01 mm (20° C.) and a specific gravity of 1.0252 (20/20° C.). Technical grades of dipropylene glycol will contain an appreciable amount of water (e.g., about 0.01 to about 0.1 wt. %). Therefore, if fresh technical grade dipropylene glycol were introduced directly into the column 100, a substantial amount of undesired contaminating water would also be introduced.

In like fashion, when propylene oxide reacts with dipropylene glycol to form tripropylene glycol, a mixture of isomeric tripropylene glycol isomers will be formed.

Accordingly, the mixture of polyoxypropylene glycols that is used as an extractive distillation agent in accordance with the present invention may be defined as a mixture having the formula:

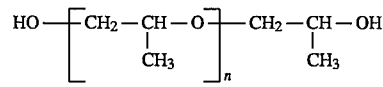

wherein n is a positive integer having a value of 1 to about 4, the mixture having an average molecular weight of less than about 250 and conveniently about 180 to 220.

When the extractive distillation process of the present invention is to be practiced on a continuous basis, the mixture of polyoxypropylene glycols can be formed in situ by initially charging propylene glycol or a lower molecular weight polyoxypropylene glycol such as dipropylene glycol or tripropylene glycol to the extractive distillation tower. Thereafter, propoxylation of the initially charged glycol will occur, as described above and over the passage of time, (e.g., about 100 hours of continuous operations) a mixture of polyoxypropylene glycols will be formed that will have the composition described above.

Alternately, a mixture of polyoxypropylene glycols having the composition described above may be formed separately (e.g., in a holding tank) and then used as the initial and recirculating extractive distillation agent.

During prolonged continuous operations of about 1,000 hours or more, and because of upsets in the extractive distillation column, the amount of heavier polyoxypropylene glycols having a molecular weight in excess of about 300 will tend to increase to an extent such that the efficiency of the continuous extractive distillation operation deteriorates. When undesirably high levels of contaminants appear in the purified propylene oxide product, the problem can be solved by purging all or part of the extractive distillation agent from the system.

Thus, when conducting continuous distillation operations in accordance with the preferred embodiment of the present invention, from about 0.1 to about 15 vol. % per hour of the total volume of circulating solvent is removed and replaced with an equivalent volume of fresh solvent, the amount being adjusted to provide a circulating stream of solvent having an average molecular weight of not more than about 250, such as an average molecular weight of about 180 to about 220.

BRIEF DESCRIPTION OF THE DRAWING

The drawing is a schematic flow sheet with conventional parts omitted showing the general recovery sequence that is used in accordance with the present invention in purifying propylene oxide.

In the drawing, for convenience, the present invention is illustrated in connection with a process wherein the propylene oxide is prepared by the epoxidation of propylene with tertiary butyl hydroperoxide in solution in tertiary butyl alcohol to provide a reaction product comprising propylene oxide and additional tertiary butyl alcohol.

DESCRIPTION OF THE PREFERRED EMBODIMENT

Turning now to the drawing, there is shown a schematic flow sheet illustrating a preferred method of practicing the process of the present invention. In the drawing, conventional parts such as valves, pumps, temperature sensors, pressure sensors, heaters, coolers, flow control regulation apparatus, etc., have been omitted.

In accordance with a preferred embodiment of the present invention, propylene oxide is separated in a preliminary distillation zone (not shown) from other components of an epoxidation reaction mixture in order to provide an impure propylene oxide fraction contaminated with oxygen-containing impurities such as acetone, methanol, water, etc.

The impure propylene oxide feedstock that is thus obtained in the preliminary distillation zone is then purified in a propylene oxide purification distillation zone, which in accordance with the preferred embodiment of the present invention, comprises two distillation columns, each of which is equipped with an appropriate reflux condensing means and an appropriate reboiler heating means.

In accordance with the present invention, an impure propylene oxide feedstock fraction, such a fraction contaminated with from about 50 to about 4,000 ppm of methanol, from about 0.01 to about 2 wt. % of acetone and about 0.01 to about 2 wt. % of water and other oxygen-containing impurities, is charged by way of a line 120 leading to a distillation column 100 which, in accordance with the present invention, will preferably be a column containing at least about 10 theoretical plates, more preferably at least 25 theoretical plates and still more preferably, from about 30 to about 100 theoretical plates. The column 100 is suitably operated under distillation conditions including a pressure of about 10 to 40 psia, a reflux ratio of from about 2:1 to about 10:1, a reboiler temperature within the range of about 100° to about 250° C. (e.g., 210° C.) and a top temperature of about 20° to about 80° C. (e.g., about 20° C.).

The impure propylene oxide is preferably charged to the distillation column 100 in the lower half thereof. An extractive distillation agent comprising a mixture of polyoxypropylene glycols is charged to the upper half of the distillation column 100 by an extractive distillation charge line 106.

An essentially anhydrous purified propylene oxide fraction, such as a fraction containing about 100 ppm or less of water is removed from the column 100 as a light distillation fraction 112, the purified propylene oxide in the line 112 containing significantly reduced amounts of methanol and acetone, such as about 15 to 900 ppm of methanol and about 0.1 to 100 ppm of acetone. A heavier fraction 110 is withdrawn from the distillation column 100 which contains substantially all of the extractive distillation agent charged by the line 106 and also substantially all of the water, acetone and other oxygen-containing impurities introduced into the column 100 with the impure propylene oxide 120.

The heavier distillation fraction 110 from the column 100 comprising water, methanol, acetone, tertiary butyl alcohol and other impurities and extractive distillation agent is charged to a second distillation column 200 wherein light impurities such as methanol, acetone, water, etc., are separated overhead as a distillation fraction 204 that is discharged from the system for any suitable use, such as for use as a steam boiler feedstock or for recovery.

A heavier distillation fraction 106 is discharged from the distillation column 200 comprising a mixture of polyoxypropylene glycols which is recycled to distillation column 100 by line 106.

In accordance with the present invention, fresh extractive distillation agent, either as the original charge, or as make-up solvent, is introduced into the system by a branch line 230 leading to the charge line 110 for the second distillation column 200 so that any water introduced into the system with the fresh extractive distillation agent will be separated therefrom in the column 200 and withdrawn from the column 200 through the line 204.

Thus, for example, at the start of continuous operations, an initial charge of propylene glycol or dipropylene glycol may be charged to the system by the line 230. As the initial charge of propylene glycol or dipropylene glycol circulates through the extractive distillation column 100, a reaction of propylene oxide with the initial charge will occur and as a consequence, within about 100 hours of operation, the desired mixture of polyoxypropylene glycols will be formed, in situ. Alternately, a mixture of polyoxypropylene glycols having the characteristics described above may be prepared outside of the distillation column 100 (e.g., in a holding tank, not shown) and then charged to the system by the line 230.

When an undesirable concentration of polyoxypropylene glycols having a molecular weight of more than about 300 builds up in the line 106, all or part of the circulating stream of extractive distillation agent may be purged from the system through a purge line 240 controlled by a normally closed valve 242 and replaced with fresh extractive distillation agent charged by way of line 230.

EXAMPLE

The invention will be further illustrated by the following specific examples which are given by way of illustration and not as limitations on the scope of this invention. Where parts are mentioned, they are parts by weight.

A two-inch Oldershaw-type distillation column containing 120 actual trays was used in an extractive distillation to remove oxygenated impurities from a crude propylene oxide feed stream. The purified propylene oxide was recovered as the overhead product from this first column, and the solvent plus impurities made up the bottoms stream. A second one-inch stainless steel column packed with eleven feet of stainless steel wire mesh packing, was used to purify the contaminated solvent which was then recycled from the bottoms of the second column to a point above the feed on the first column. The impurities removed from the solvent were recovered in the overhead of the second column. The solvent used was di-propylene glycol. A 14-day run was made where an initial amount of solvent was charged to the columns and tankage. During the run, no solvent was purged from or added to the system. Table 1 shows the composition of the crude propylene oxide feed and the purified product at various points during the run. Table 2 shows the composition of the solvent at the beginning and during the run.

TABLE 1

| | Feed and Product Compositions | | | |
|---|---|---|---|---|
| | Crude PO Feed | PO Product at 112 Hrs | PO Product at 224 Hrs | PO Product at 336 Hrs |
| Water (ppm) | 1100 | 98 | 94 | 84 |
| Methanol (ppm) | 400 | 190 | 170 | 190 |

TABLE 1-continued

Feed and Product Compositions

|  | Crude PO Feed | PO Product at 112 Hrs | PO Product at 224 Hrs | PO Product at 336 Hrs |
|---|---|---|---|---|
| Acetone (ppm) | 2400 | <1 | <1 | <1 |

TABLE 2

Solvent Composition

|  | Initial Composition | Composition at 112 Hrs. | Composition at 224 Hrs. | Composition at 336 Hrs. |
|---|---|---|---|---|
| DPG (wt. %) | 99 | 79 | 64 | 54 |
| DPG + 1 PO (wt %) | 0 | 18 | 30 | 36 |
| DPG + 2 PO (wt %) | 0 | 2.0 | 5.5 | 8.7 |
| DPG + 3 PO (wt %) | 0 | 0.25 | 0.69 | 1.4 |

Water and oxygen-containing impurities such as acetone and methanol are difficult to remove from propylene oxide by standard distillation. The use of an extractive distillation agent consisting essentially of a mixture of polyoxypropylene glycols, as described above, in an extractive distillation column improves the separation of these impurities from propylene oxide.

Having thus described our invention, what is claimed is:

1. An extractive distillation process for the distillation of impure propylene oxide feedstock in an extractive distillation column to remove oxygenated contaminants, including water, methanol and acetone from the impure propylene oxide which comprises the steps of:

introducing said impure propylene oxide feedstock into the lower half of an extractive distillation column, introducing an extractive distillation agent consisting essentially of a mixture of polyoxypropylene glycols into said extractive distillation column above the point of introduction of said impure propylene oxide feedstock, said extractive distillation agent being introduced into said extractive distillation column in the ratio of feedstock to said extractive distillation agent of from about 1:1 to about 20:1, withdrawing a lighter distillation fraction from said extractive distillation column consisting essentially of essentially anhydrous propylene oxide contaminated with reduced quantities of said methanol, withdrawing a heavier distillation fraction from said extractive distillation column containing substantially all of the polyoxypropylene glycols, acetone and water and a portion of the methanol introduced into said extractive distillation column, the extractive distillation agent consisting essentially of a mixture of polyoxypropylene glycols having the formula:

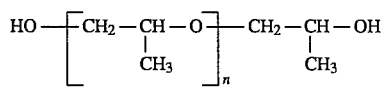

wherein n is a positive integer having a value of 1 to about 4, the mixture having an average molecular weight of about 180 to about 220.

2. An extractive distillation process for the distillation of impure propylene oxide feedstock in an extractive distillation column fitted with a reboiler and a reflux condenser to remove oxygenated contaminants, including water, methanol and acetone from the impure propylene oxide which comprises the steps of:

introducing said impure propylene oxide feedstock into the lower half of an extractive distillation column containing at least 25 theoretical plates, introducing an extractive distillation agent consisting essentially of a mixture of polyoxypropylene glycols into said extractive distillation column at a point at least 4 theoretical plates above the point of introduction of said impure propylene oxide feedstock, said extractive distillation agent being introduced into said extractive distillation column in the ratio of feedstock to said extractive distillation agent of from about 1:1 to about 20:1, withdrawing a lighter distillation fraction from said extractive distillation column consisting essentially of essentially anhydrous propylene oxide contaminated with reduced quantities of said acetone and methanol, fractionating said impure propylene oxide feedstock in said extractive distillation column under distillation conditions including a pressure of about 10 to 40 psia, a reflux ratio of from about 1:1 to about 5:1 and a reboiler temperature within the range of about 100° to about 250° C. and a top temperature of about 20° to about 80° C., withdrawing a heavier distillation fraction from said extractive distillation column containing substantially all of the polyoxypropylene glycols, a portion of the acetone and water and a portion of the methanol introduced into said extractive distillation column, the extractive distillation agent consisting essentially of a mixture of polyoxypropylene glycols having the formula:

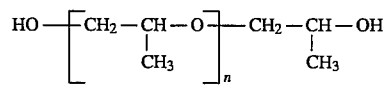

wherein n is a positive integer having a value of 1 to about 4, the mixture having an average molecular weight of about 180 to about 220.

3. An extractive distillation process for the continuous distillation of impure propylene oxide feedstock in an extractive distillation column fitted with a reboiler and a reflux condenser to remove oxygenated contaminants, including water, methanol and acetone from the impure propylene oxide which comprises the steps of:

continuously introducing said impure propylene oxide feedstock into the lower half of an extractive distillation column containing at least 25 theoretical plates, continuously introducing an extractive distillation agent consisting essentially of a mixture of polyoxypropylene glycols into said extractive distillation column at a point at least 4 theoretical plates above the point of introduction of said impure propylene oxide feedstock, said extractive distillation agent being introduced into said extractive distillation column in the ratio of feedstock to said extractive distillation agent of from about 1:1 to about 20:1, continuously fractionating said impure propylene oxide feedstock in said extractive distillation column under distillation conditions including a pressure of about 10 to 40 psia, a reflux ratio of from about 1:1 to about 5:1, a reboiler temperature within the range of about 100° to about 250° C. and a top temperature of about 20° to about 80° C.

continuously withdrawing a lighter distillation fraction from said extractive distillation column consisting essentially of essentially anhydrous propylene oxide contaminated with reduced quantities of said methanol, continuously withdrawing a heavier distillation fraction from said extractive distillation column containing substantially all of the polyoxypropylene glycols, acetone and water and a portion of the methanol introduced into said extractive distillation column, continuously charging said heavier distillation fraction to a distillation column and separating it therein into a lighter distillation fraction comprising water, acetone and methanol and a heavier distillation fraction comprising said mixture of polyoxypropylene glycols, and continuously recycling said heavier distillation fraction to said extractive distillation column as said extractive distillation agent, the extractive distillation agent consisting essentially of a mixture of polyoxypropylene glycols having the formula:

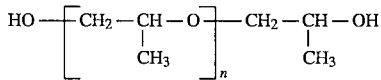

wherein n is a positive integer having a value of 1 to about 4, the mixture having an average molecular weight of about 180 to about 220.

4. An extractive distillation process for the continuous distillation of impure propylene oxide feedstock in an extractive distillation column fitted with a reboiler and a reflux condenser to remove oxygenated contaminants, including water, methanol and acetone from the impure propylene oxide which comprises the steps of:

continuously introducing sad impure propylene oxide feedstock into the lower half of an extractive distillation column containing at least 25 theoretical plates operated under distillation conditions including a pressure of about 10 to 40 psia, a reflux ratio of from about 1:1 to about 5:1, a reboiler temperature within the range of about 100° to about 250° C. and a top temperature of about 20° to about 80° C., introducing an initial extractive distillation agent charge consisting essentially of propylene glycol or dipropylene glycol into said extractive distillation column at a point at least 4 theoretical plates above the point of introduction of said impure propylene oxide feedstock, said extractive distillation agent being introduced into said extractive distillation column in the ratio of feedstock to said extractive distillation agent of from about 1:1 to about 20:1, continuously circulating said initial charge through said extractive distillation column whereby said initial charge will be propoxylated and form a mixture of polyoxypropylene glycols, continuously fractionating said impure propylene oxide feedstock in said extractive distillation column, continuously withdrawing a lighter distillation fraction from said extractive distillation column consisting essentially of essentially anhydrous propylene oxide contaminated with reduced quantities of said acetone and methanol, continuously withdrawing a heavier distillation fraction from said extractive distillation column containing substantially all of the polyoxypropylene glycols and water and a portion of the acetone and methanol introduced into said extractive distillation column, continuously charging said heavier distillation fraction to a distillation column and separating it therein into a lighter distillation fraction comprising water, acetone and methanol and a heavier distillation fraction comprising said mixture of polyoxypropylene glycols, and continuously recycling said heavier distillation fraction to said extractive distillation column as said extractive distillation agent, the extractive distillation agent consisting essentially of a mixture of polyoxypropylene glycols having the formula:

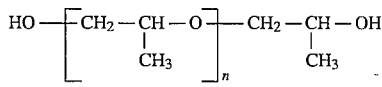

wherein n is a positive integer having a value of 1 to about 4, the mixture having an average molecular weight of about 180 to about 220.

5. An extractive distillation process for the continuous extractive distillation of impure propylene oxide in an extractive distillation column fitted with a reboiler and a reflux condenser to remove oxygenated contaminants, including about 0.01 to 2 wt. % of water, from about 50 to about 4,000 ppm of methanol and from about 0.01 to about 2 wt. % of acetone from the impure propylene oxide which comprises the steps of:

continuously introducing said impure propylene oxide feedstock into the lower half of a first extractive distillation column containing from about 30 to 120 theoretical plates operated under distillation conditions including a pressure of about 10 to 40 psia, a reflux ratio of from about 1:1 to about 5:1, a reboiler temperature within the range of about 100° to about 250° C. and a top temperature of about 20° to about 80° C., introducing an initial extractive distillation agent charge comprising propylene glycol or dipropylene glycol into said first extractive distillation column at a point from about 7 to about 50 theoretical stages above the point of introduction of said impure propylene oxide feedstock, said extractive distillation agent being introduced into said first extractive distillation column in the ratio of feedstock to said extractive distillation agent of from about 2:1 to about 10:1, continuously circulating said initial charge through said first extractive distillation column whereby said initial charge will be propoxylated and form a mixture of polyoxypropylene glycols, continuously fractionating said impure propylene oxide in said first extractive distillation column, continuously withdrawing a first lighter distillation fraction from said first extractive distillation column consisting essentially of propylene oxide contaminated with about 5 to about 600 ppm of water, about 15 to 2,000 ppm of methanol and about 0.1 to about 100 ppm of acetone, continuously withdrawing a first heavier distillation fraction from said first extractive distillation column containing substantially all of the polyoxypropylene glycols and water and a portion of the acetone and methanol introduced into said extractive distillation column, continuously charging said first heavier distillation fraction to a second distillation column and separating it therein into a second lighter distillation fraction comprising water, acetone and methanol and a second heavier distillation fraction comprising said mixture of polyoxypropylene glycols, continuously purging from about 0.1 to about 15 vol. % per hour of the total volume of extractive distillation agent from said second heavier distillation fraction, continuously recycling the remainder of said heavier distillation fraction to said extractive distillation column as said extractive distillation agent, and continuously replacing said purged volume of circulating extractive distillation agent with an equivalent volume of propylene glycol or dipropylene glycol, the polyoxypropylene glycols of said mixture of polyoxypropylene glycols having the formula:

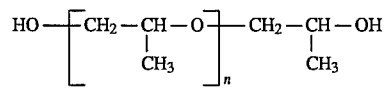

wherein n is a positive integer having a value of 1 to about 4, said mixture of polyoxypropylene glycols having an average molecular weight of about 180 to 220.

* * * * *